United States Patent
Febbroriello et al.

(10) Patent No.: US 7,166,079 B2
(45) Date of Patent: Jan. 23, 2007

(54) METHODS AND APPARATUS FOR OBSERVING AND RECORDING IRREGULARITIES OF THE MACULA AND NEARBY RETINAL FIELD

(75) Inventors: Peter Febbroriello, Torrington, CT (US); David M. Davis, Spring Mount, PA (US)

(73) Assignee: Sensory Arts & Science, LLC, Lederach, PA (US)

( * ) Notice: Subject to any disclaimer, the term of this patent is extended or adjusted under 35 U.S.C. 154(b) by 621 days.

(21) Appl. No.: 10/348,163

(22) Filed: Jan. 21, 2003

(65) Prior Publication Data

US 2003/0212310 A1   Nov. 13, 2003

Related U.S. Application Data

(60) Provisional application No. 60/351,277, filed on Jan. 23, 2002.

(51) Int. Cl.
*A61B 13/00* (2006.01)
(52) U.S. Cl. .................................. 600/558
(58) Field of Classification Search ........... 600/558; 351/7, 211, 246, 247, 23, 222, 200, 223, 243; 348/14.16, 14.01; 313/478; 359/296; 372/109; 385/93
See application file for complete search history.

(56) References Cited

U.S. PATENT DOCUMENTS

| | | | |
|---|---|---|---|
| 3,982,828 A | 9/1976 | Woolf | 351/23 |
| 3,992,087 A | 11/1976 | Flom et al. | 351/7 |
| 4,541,697 A | 9/1985 | Remijan | 351/211 |
| 4,545,658 A | 10/1985 | Weiss | 351/222 |
| 5,646,710 A * | 7/1997 | Caskey | 351/223 |
| 5,953,052 A * | 9/1999 | McNelley et al. | 348/14.16 |
| 5,953,102 A | 9/1999 | Berry | 351/247 |
| 6,315,412 B1 | 11/2001 | Snodderly et al. | 351/200 |
| 6,386,707 B1 | 5/2002 | Pellicano | 351/246 |
| 2003/0053513 A1 * | 3/2003 | Vatan et al. | 372/109 |

* cited by examiner

*Primary Examiner*—Max F. Hindenburg
*Assistant Examiner*—Brian Szmal
(74) *Attorney, Agent, or Firm*—Woodcock Washburn LLP

(57) ABSTRACT

Systems and methods for observing and recording retinal irregularities are disclosed. A method according to the invention includes illuminating a viewing area with a steady light, illuminating the viewing area with a flash pattern, and enabling a user to observe, by looking at the illuminated viewing area, a visual representation of the existence of a retinal irregularity. The viewing area is illuminated with the steady light and flash pattern such that the user can identify in the viewing area a visual abnormality that is indicative of the retinal irregularity. The user can provide a description of the visual representation, which can be forwarded to a caregiver for analysis.

16 Claims, 2 Drawing Sheets

METHODS AND APPARATUS FOR OBSERVING AND RECORDING IRREGULARITIES OF THE MACULA AND NEARBY RETINAL FIELD

CROSS-REFERENCE TO RELATED APPLICATIONS

This application claims priority from Provisional U.S. Patent Application No. 60/351,277, filed Jan. 23, 2002, the contents of which are hereby incorporated by reference.

FIELD OF THE INVENTION

The invention relates to systems and methods that enable a person to observe and record irregularities and defects in the macula, and in certain instances, the surrounding retinal area of the eye. These defects are most often a result of Age-related Macular Degeneration (AMD), but may also occur as a result of other diseases and conditions, such as Diabetic Retinopathy, Macular Edema, macular hole formation, presence of a foreign body or growth, among others.

BACKGROUND OF THE INVENTION

The macula is responsible for sharpness of the central visual field. Various conditions, such as Macular Degeneration, are caused by occlusion and defects in the macular surface and substrate. Most early detection methods rely on an advanced state of degeneration such as significant drusen, growth of abnormal and potentially leaky blood vessels, or even macular hole formation in order to detect the presence of the condition.

While there are many promising therapeutics that may arrest or even repair the degenerative condition, there are currently no simple and accurate methods for early detection and monitoring the condition without an ophthalmic exam. It is therefore evident that a way to detect macular irregularities while still in their very early stage of development, and provide a vehicle to monitor the characteristics of the irregularities is a highly desirable way to potentially reduce the incidence and severity of this situation.

The well-known Amsler grid is generally acknowledged as the patient's main way of detecting early central vision abnormalities and macular deformations. However, the Amsler Grid has not been shown to always be accurate and therefore effective, and may only be valuable in determining vision impairment when the condition has reached a fairly advanced stage of development. A method is needed that will facilitate the earliest possible detection of central visual impairment, while therapeutic treatments and regimens can be most effective.

SUMMARY OF THE INVENTION

The invention provides systems and methods for detecting retinal irregularities such as macular degeneration, diabetic retinopathy, macular edema, macular hole formation, and various other abnormalities that result in a stress or sensitivity change of the retina. A method according to the invention includes illuminating a viewing area steadily and with a flash pattern, and enabling a user to detect, by looking at the illuminated viewing area, the existence of retinal irregularities. The flash pattern can be defined by at least one of a color, a repetition frequency, and a duty cycle. The user can be enabled to define the flash pattern and/or to select the flash pattern from among a plurality of predefined flash patterns. Parameters that define the flash pattern can be stored and retrieved for subsequent use.

To detect the existence of the retinal irregularity, the viewing area is illuminated both by a steady light source, and with a flash pattern such that the user can identify in the viewing area a visual perturbation that is indicative of the retinal irregularity. The user can provide a description of the visual perturbation, which can be forwarded to a caregiver for analysis. The user can then be provided with an analysis by the caregiver of the visual perturbation.

A software embodiment of the invention includes a computer-readable medium according to the invention has stored thereon computer-executable instructions for performing such a method for detecting a retinal irregularity.

A device implementation of the system according to the invention includes a power supply, light source, light source modulator or timing circuit, and diffusion mechanism in order to properly deliver the necessary test capability. As such, the device embodiment may be electrical, electro-mechanical, or mechanical in nature.

BRIEF DESCRIPTION OF THE DRAWING

Other features of the present invention are further apparent from the following detailed description of the embodiments of the present invention taken in conjunction with the accompanying drawing, of which.

DETAILED DESCRIPTION OF ILLUSTRATIVE EMBODIMENTS

Figure 1:
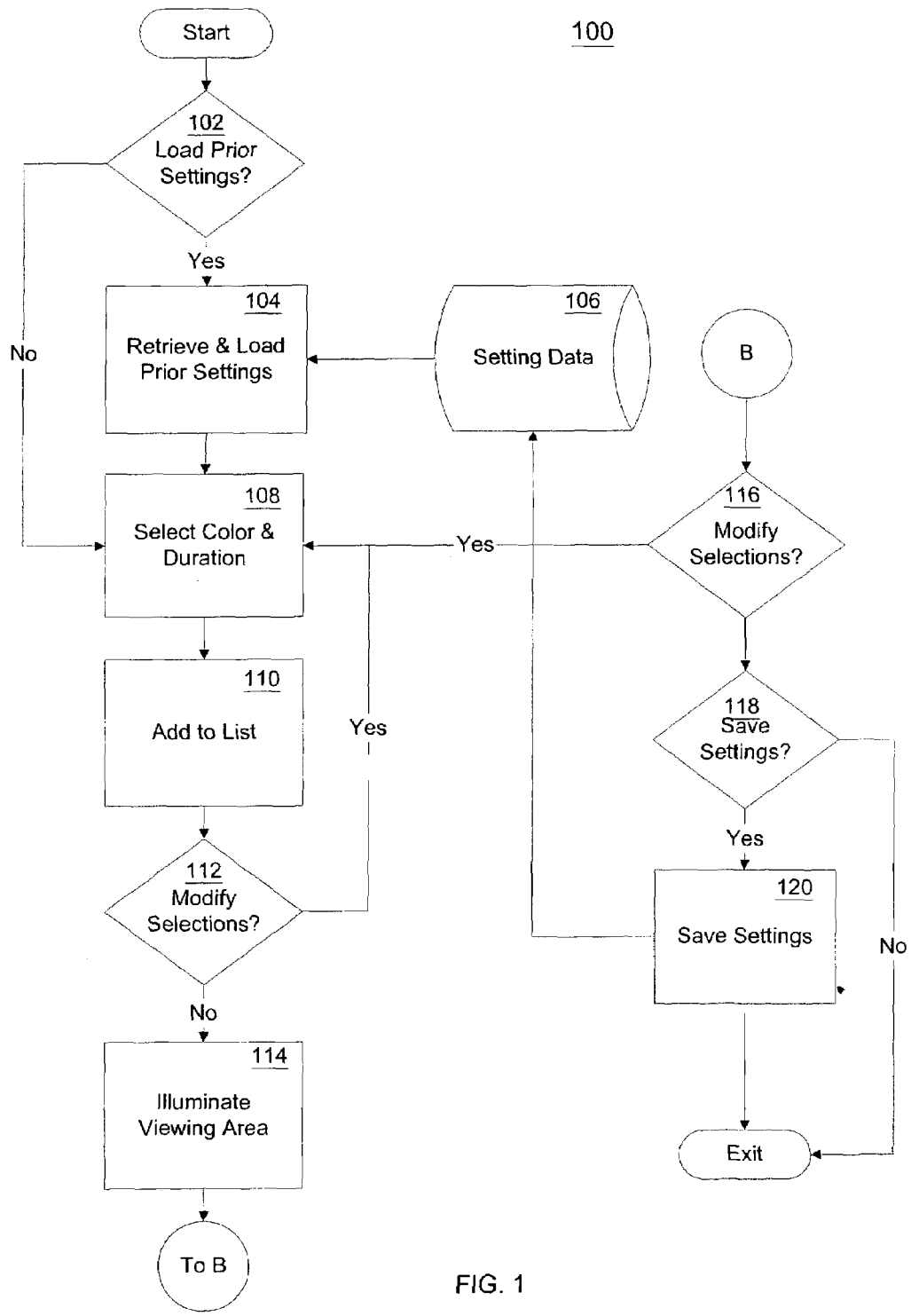
FIG. 1 is a flowchart of a preferred embodiment of a method according to the invention.

The invention relates to methods and assistive technology that enable the patient or user to observe the abnormalities and physiological defects in the macular region and surrounding area of the retina, and record them for subsequent evaluation by a caregiver and comparison over time.

According to the invention, the well-known rhodopsin bleach/recovery cycle of the rods and cones of the retina, and particularly of the macular area, in conjunction with downstream retina/brain visual processing can be synchronized with an external illumination or flashing light source that provides an enhanced ability of the user to observe retinal irregularities including a persistence of vision state in which the user can continuously observe certain defects or irregularities present, and record them for further evaluation.

A method for making the defects visible to the patient by a cycle synchronous with the rhodopsin bleach/recovery timing can be performed without any apparatus at all, but would rely on the user to consistently blink or manually occlude an illuminated viewing area with a frequency and duration that is both difficult to establish and to maintain. It is therefore desirable to provide apparatus that facilitates and can replicate and maintain the process state in order to achieve the persistence of vision effect that enables to user to clearly view the abnormalities and describe or illustrate them for subsequent review and comparison, as necessary, by a caregiver.

The viewing process includes one or more steps. First, the user looks directly at the illuminated surface or screen, then moves the eyes left, right, up, and down in any sequence, thereby scanning the visual field area for flashes or defects evidencing abnormalities. Then, the illumination is modulated while the user looks steadily at the center of the screen or illuminated surface. Finally, with the illuminated viewing area still modulated, the user again moves their eyes in the right, left, up, and down position to further view any irregularities. These steps can be performed in any order.

During these steps, the prolonged visualization phenomenon may occur, thereby enabling the user to clearly observe the irregularities for a period of time.

Once any present defects or irregularities are observable in a persistent manner, the patient or user can then describe the irregularities in a verbal, written, or pattern recognition mode as recorded evidence of the abnormalities.

In these instances, the user may actually be viewing the very early stages of the macular degeneration and/or irregularities in the macula or nearby retinal region forming or beginning to occur. The patterns observed are evidence of the abnormalities, occurring in areas of the retina that are under stress or have increased or diminished sensitivity from physical damage, or if the rhodopsin bleach/recovery cycle is compromised. In any of these situations, there may be visual signatures that can be observed by the user.

The ability of the patient to observe and record the current state of the macular and retinal irregularities can be valuable in monitoring the condition over the course of treatment or therapeutic regimen, based on any of a plurality of methods and substances.

The irregularities may appear as any of a plurality of artifacts or visual signatures. For instance, a stress or strain of sufficient force on the retina, there may appear a flash of light. If stresses are extreme, and retinal damage occurs, the damage may visualize as a dark area. Early image patterns seen may include circles or crescents of light, sometimes with a wavy border, or with a diffuse halo. A bulls-eye pattern, with a dark spot in the center, may evidence a macular hole formation. A healing hole may appear as a dark cross on a light background, as tissue fills in the damaged area.

Because the retina and brain work together, and visual fusion may mask or merge images on the retina, the irregularities may only be visible during very brief periods such as when the observer blinks, moves the eye directionally, or when an illumination flash occurs. Achieving the visualization accidentally would allow observation of a transient image for only a small fraction of a second, and cluttered backgrounds would make the defect visible only during brief transition periods when conditions were exactly right.

It may be important for retinal abnormalities to be diagnosed even when the defect is still "pre-clinical" or when the damage is still sufficiently minor that the normal correctional abilities of the body can be brought into play. Since a small decrease of sensitivity my take place during the early stages of AMD or macular hole formation, this minor loss might be visualized if conditions could be found to take advantage of the timing of retinal/brain signal processing so as to bypass the brain's compensation and corrective stages of image processing. Also, if the rhodopsin bleach/recovery cycle were compromised, this would also appear as reduced sensitivity. By using a pulse of illumination followed by a period of darkness, one could synchronize the period of illumination and darkness with the signal processing chain and the rhodopsin bleach/recovery cycle so as to take advantage of the window of opportunity that exists on the edge of each cycle. If a pulse of illumination with a brief duration, say 50 milliseconds were used, the subject would see a brief image of the defect. A longer illumination period would result in the subject seeing the image of the defect for a brief period, followed by immediate fading and disappearance of the image of the defect as brain and retina make instant corrections to improve the visual field. A dark period of up to perhaps 200 milliseconds allows for rhodopsin recovery, which is then followed by another light pulse. By repeating the pulse sequence, the correctional process is abated and the image lingers such that it can be seen continuously. Repetition rates up to 15 Hz generally produce a very clear image that is persistent, and can therefore be studied and described.

Apparatus according to the invention can include any light source that can be modulated to provide an alternating flash sequence of varying duration, duty cycle, and color complement. By allowing the user to modify the characteristics of the flash sequence, the user can 'tune' the sequence to best match the rhodopsin refresh cycle of the macula, and therefore optimize the persistence of the visible defect for an extended period of time.

Once visible, the user can then articulate the shape and location of the perceived irregularities by rendering them on a drawing, with a pointing device on a computer screen, or by selecting a representative rendering from a list of illustrations prepared in advance.

In a microprocessor-based embodiment, the rendering of the abnormalities can then be stored for subsequent comparison, and printed or transmitted from the device to another location via the Internet or other direct or indirect connection.

Preferably, the user should be situated in a setting where there is no reflective light source that might create a glare on the viewing screen or surface. The user can then load the program or turn on the device. If this is the first time using the apparatus, default values may be loaded, such as a pattern of steady white (255,255,255 RGB (red green blue) values), which is provided for a first period of time, followed by a flash pattern consisting of 50 milliseconds white followed by 200 milliseconds of black (0,0,0 RGB values). Once the user then chooses to begin display of the flash pattern, it continues until stopped by the user.

Covering one eye at a time, the user then looks directly at the screen or viewing area, at a close enough distance to substantially encompass their entire field of vision. During the steady white light interval, the user gazes directly at the viewing area, then moves the eye directionally at a moderate or variable pace, observing for flashes or other effects which are seen each time the eye comes to a stop at the end of the directional movement. The flashes or other effects that the user perceives are indicative of a macular or other such optical defect. The continuous flash pattern will also cause the macular defects to become visible, since strained or damaged cells will process light at a different pace than the normal substrate. In order to improve the visibility of the defect(s), the user may alter the flash pattern values dynamically, thereby tuning the settings to optimize their ability to most clearly visualize the defects.

Observed irregularities and patterns may then be recorded by the user on a paper document, or drawn on a computer screen with a mouse, stylus, or similar pointing device. In the alternative, a series of sample illustrations may be provided so the user can choose from a list rather than having to draw the observed irregularities. Once recorded, the results of the test can be printed or transmitted and reviewed by an eye-care professional in order to assess the results and recommend a course of treatment if necessary.

Prior to exiting the program or turning the device off, the user may be prompted to save any settings and annotations, if applicable.

FIG. 1 is a flowchart of a preferred embodiment of a method 100 for observing a retinal irregularity. A computer-readable medium having computer-executable instructions stored thereon for performing such a method can be embodied, for example, as or in a Personal Computer, Personal Digital Assistant, Internet Appliance, CD or DVD player, cell phone, and other similarly capable device that can read and render the capabilities described on a viewing device or external viewing area. Such a device could include a microprocessor, input keyboard and/or pointing device, storage, and display.

Preferably, the invention allows for storage and retrieval of prior settings and other pertinent data to be maintained for continuity between sessions. At step 102, the user is asked whether previously stored settings should be retrieved and loaded. If so, the settings are retrieved and loaded at step 104. This may be accomplished within the software via file input/output operations that allow a plurality of file types to be used, any or all of which may contain parameters that specify the range of and recent specific illumination possible values, and user specific values as previously saved and stored. These files may be located on the device being used for the test, or retrieved from a remote device via a synchronous or asynchronous connection. File contents include setting data 106 corresponding to parameters that uniquely identify the user, possible settings, and recent settings of instructions that govern the illumination brightness and consistency, flash pattern colors, frequency, and duty cycle. These parameters may vary based on the device implementation, given possible variance in the screen display, processor, and other device attributes that may cause the pattern to be displayed differently.

In order to provide an optimal viewing state for the user, color and flash pattern (which includes duty cycle and repetition frequency) may be specified at step 108. The user, or party responsible for configuring the settings may select a color and duration from a list of available choices. The color may be specified as the Red, Green, and Blue values that combine to represent a color, or a color palette may display choices. Duration of subsequent display of the color may be entered as an integer value in units, typically milliseconds, or may be selected from a list of choices. A list of predefined patterns can be provided, thus enabling the user or person configuring the system to select from a set of predefined patterns. Alternatively, the user can define a new pattern. The pattern can be chosen or defined by the user or person responsible for configuring the display.

At step 110, the user, or party responsible for configuring the settings may specify an action to add the selected color/duration entry to a list of temporarily saved choices. This list of color/duration choices becomes the pattern for subsequent delivery to the user of the embodiment.

At step 112, the user is given an option to modify the selected options. If, at step 112, the user elects to modify the selected options, the system returns to step 108 and enables the user to redefine or reselect color and flash pattern parameters.

Once a pattern is chosen, a specific action is offered, at step 114, whereby the user can cause the system to begin to illuminate the viewing surface. Preferably, the viewing surface is first illuminated with a steady light (e.g., white light) for a first period of time, and then illuminated with the selected flash pattern for a second period of time. The viewing of the steady light and flash pattern facilitates the observation of macular and retinal abnormalities if there exists a variation in the sensitivity of the retina in that area. Any variation in the sensitivity of the retinal or macular strata, be it a thinning, thickening, pull, push, disease artifact, foreign body presence, or aberration in the rhodopsin bleach/recovery cycle causes variation in the sensitivity of the retinal surface, and therefore affects that portion of the visual field. Preferably, the viewing surface is a smooth, uniform, untextured surface that is free of defects that might interfere with or distract from the visual representation that the viewer would see if a retinal irregularity were to exist.

The user or person responsible for configuring the pattern may choose to modify the color and duration settings, in order to change the flash pattern. This is accomplished, at step 116, by adding, removing, or modifying entries made in the Select Color/Duration step 108, and thereby altering the list created previously at step 110. This activity can be performed repeatedly in order to find the best pattern for viewing and observing the irregularities present.

At step 118, the user or person responsible for configuring the system may select an option to store the current settings and other pertinent information to an external, permanent file for subsequent retrieval and re-use. If such option is selected, the settings are stored at step 120.

Optionally, the program may accept user annotations or pre-established diagrams of commonly occurring patterns for describing the artifacts viewed. These annotations or choice of matching patterns would be entered by a mouse, stylus, or other pointing device and drawn on the screen by the user, or selected from a list of choices.

Figure 2:
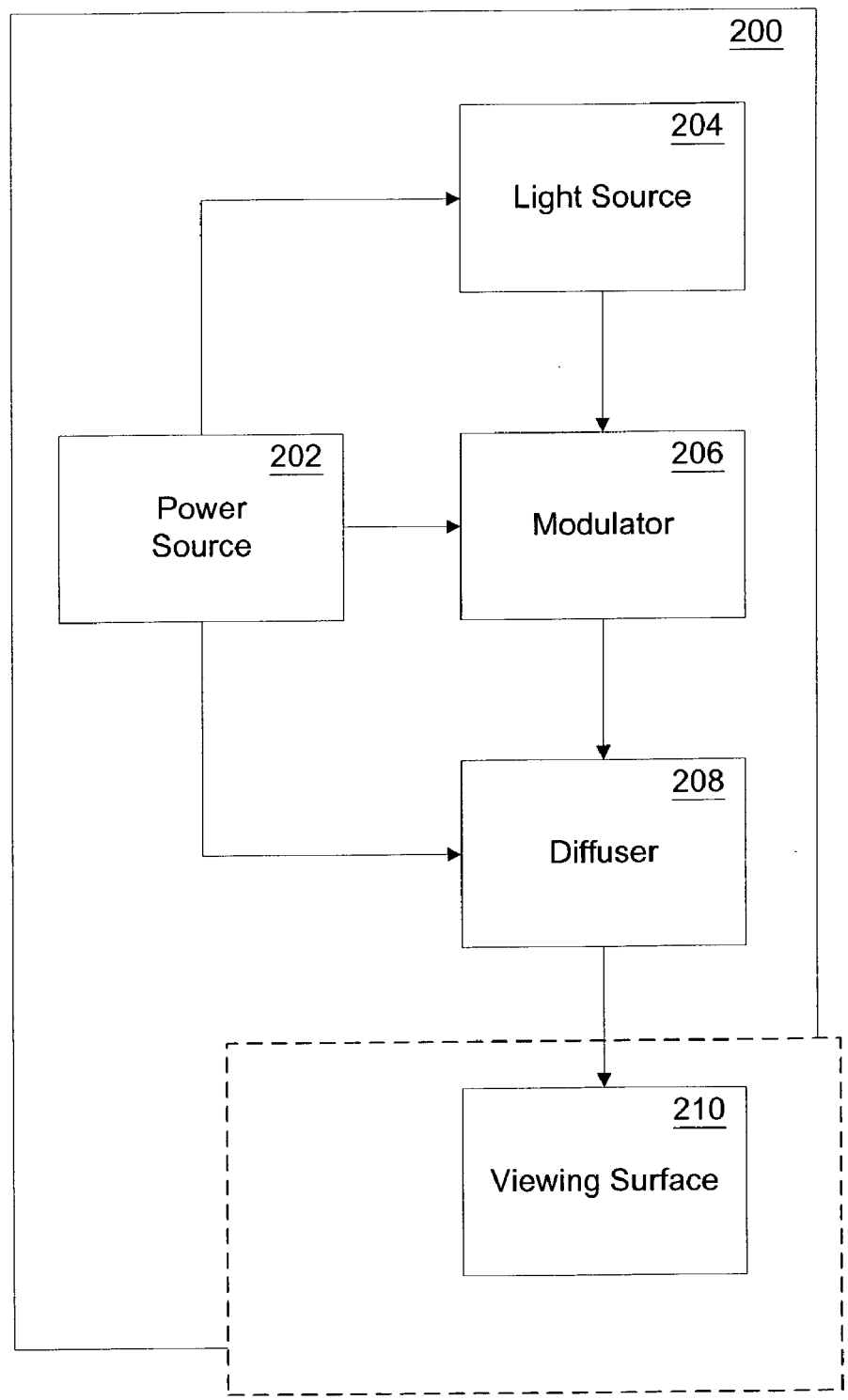
FIG. 2 depicts a preferred embodiment of a device according to the invention.

FIG. 2 is a diagram of an apparatus embodiment according to the invention. Such a device 200 can be a hand-held or stationary device that includes a power source, light source, light source modulator, diffusion mechanism, and viewing surface or area, which may be internal or external to the device. Though the preferred embodiment may be electrical, other reasonable implementations can be achieved with electro-mechanical or purely mechanical devices.

Power source 202 acts to supply alternating or direct current to the other components of the device. The power may be provided by any practical source, such as a cell or battery, solar cell, or mains current converted by a transformer and rectifier to a suitable level of DC voltage and current. In a mechanical embodiment of the device, the power source may be a wound spring, or other such mechanism to provide an energy store that may subsequently be released and modulated by the timing mechanism in 206.

A light source 204 is required to provide adequate light to create the illumination field for the device. The light source may require the power provided by the power source to deliver the necessary energy to drive the light source. The light source may be any one of a plurality of available types, including LED (Light Emitting Diode), filament bulb, or other such electrically stimulated device that produces light when power is applied. The light source may also be external to the device 200, and may be provided by a naturally occurring source such as the sun or sky, as well as other man-made sources, by pointing the device toward the external light source to draw light that it is already being produced by another source.

To achieve certain flash patterns, the light source must be modulated as in 206. The modulator comprises a pulse generator, which may be buffered and applied to the light produced in 204. The modulator may include a timing circuit that generates a pulse train, which is fed into a pulse shaper circuit that re-generates a pulse of the proper width. This pulse may be further processed by a buffering device such as a transistor or any other suitable semiconductor or relay type device which translates the pulse output of the pulse shaper into a voltage and current suitable for use by the attached light emitting devices. Circuit control interfaces can be employed to adjust the pulse train and shape in order to provide user control of the modulation. A purely mechanical implementation of the modulator can be achieved by introducing a rotating disk with holes that provide shuttering between light and dark, the spacing of which holes are synchronized with the timing of the rotation mechanism in order to achieve the desired pulse rate and duty cycle.

The diffuser mechanism in 208 provides for a generally uniform brightness of the illumination field, free of any texture, patterns, or variations that would affect the viewing. This can be achieved by any number of optical and mechanical methods, and a typical method would utilize two or more diffusion filters of translucent material, either alone or in combination with reflective surfaces that would further diffuse the light into an evenly distributed pattern. Adding space between the diffusion filters or the indirect reflective surfaces may further enhance the diffusion and eliminate any uneven lighting caused by variance in the light source, or introduced by the modulation.

Viewing surface or screen 210 is the illuminated area that the subject will view. The subject will see a steady smooth even background of uniform brightness. The surface will be illuminated with a steady light for part of the viewing sequence, and also alternate between dark and light according to the modulating method of circuit timing or programming, or mechanical shuttering.

Other controls can provide for adjustments for cycle rate, duty cycle (on/off differential), and intensity. Such controls can be incorporated where they can be easily reached while in use. If an on/off switch or mechanism is required, it may be incorporated separately, or into an intensity control for example.

The device can be operated by viewing an illuminated screen or surface either directly, or through an optional eyepiece. After viewing the steadily illuminated surface directly, and moving the eye up, down, left, and right to scan for irregularities within the visual field, the user may then introduce and modify a flash rate and intensity so as to cause the perceived image to appear more clearly and steadily. An adjustment for the duty cycle can be used to improve clarity for viewing extremely faint defects.

The user of the device can then render a drawing or other description of the visual perturbation observed, or can choose from a series of pattern illustrations that describe common defects or irregularities of the retinal area. The system could then enable the user to forward the description of the visual perturbation to a caregiver via the Internet, or other such synchronous or asynchronous connection.

Thus, there have been described systems and methods for detecting retinal irregularities. Those skilled in the art will appreciate that numerous changes and modifications can be made to the preferred embodiments of the invention, and that such changes and modifications can be made without departing from the spirit of the invention. It is intended, therefore, that the appended claims cover all such equivalent variations as fall within the true spirit and scope of the invention.

What is claimed:

1. A method for enabling a user to observe the retinal irregularity of the user's eye, the method comprising:
    illuminating a viewing area with a steady light;
    illuminating the viewing area with a flash pattern; and
    adjusting at least one of a color, a repetition frequency, and a duty cycle of said flash pattern and/or said steady light so as to enable the user to observe, by looking at the illuminated viewing area, a visual representation of the existence of a retinal irregularity of the user's eye.

2. The method of claim 1, further comprising:
    enabling the user to select the flash pattern from among a plurality of predefined flash patterns.

3. The method of claim 1, further comprising:
    enabling the user to define at least one of the steady light and the flash pattern.

4. The method of claim 1, further comprising:
    enabling the user to store parameters that define either the steady light or the flash pattern.

5. The method of claim 1, wherein enabling the user to observe the visual representation comprises illuminating the viewing area such that the user can identify in the viewing area a visual abnormality that is indicative of the retinal irregularity.

6. The method of claim 5, further comprising:
    receiving from the user, a description of the visual abnormality.

7. The method of claim 6, further comprising:
    forwarding the description of the visual abnormality to a caregiver.

8. The method of claim 1, wherein the retinal irregularity includes at least one of macular degeneration, diabetic retinopathy, macular edema, and macular hole formation.

9. A system for enabling self-detection of a retinal irregularity, the system comprising:
    a light source that illuminates a viewing area with a steady light;
    a modulator that modulates the steady light to achieve a flash pattern at the viewing area; and
    means for enabling a user to observe, by looking at the illuminated viewing area, a visual representation of the existence the retinal irregularity.

10. The system of claim 9, wherein the light source comprises a light emitting diode.

11. The system of claim 9, wherein the modulator comprises a timing circuit that generates a pulse train.

12. The system of claim 11, wherein the pulse train is fed into a pulse shaper circuit that generates a pulse of predefined width and shape.

13. The system of claim 11, wherein the modulator comprises a rotating disk.

14. The system of claim 9, further comprising a diffuser that provides generally uniform brightness of the light.

15. The system of claim 14, wherein the diffuser comprises a plurality of diffusion filters.

16. A computer-readable medium having stored thereon computer-executable instructions for performing a method for observing a retinal irregularity, the method comprising:
    illuminating a viewing area with a steady light;
    illuminating the viewing area with a flash pattern; and
    adjusting at least one of a color, a repetition frequency, and a duty cycle of said flash pattern and/or said steady light so as to enable the user to observe, by looking at the illuminated viewing area, a visual representation of the existence of the retinal irregularity of the user's eye.

* * * * *